(12) United States Patent
Spindler et al.

(10) Patent No.: US 10,188,487 B2
(45) Date of Patent: Jan. 29, 2019

(54) DENTAL IMPLANT SUPERSTRUCTURE SUPPORT

(71) Applicants: Bruno Spindler, Oppenau (DE); Curd Gadau, Bessenbach (DE)

(72) Inventors: Bruno Spindler, Oppenau (DE); Curd Gadau, Bessenbach (DE)

( * ) Notice: Subject to any disclaimer, the term of this patent is extended or adjusted under 35 U.S.C. 154(b) by 221 days.

(21) Appl. No.: 14/997,489

(22) Filed: Jan. 16, 2016

(65) Prior Publication Data

US 2016/0206408 A1  Jul. 21, 2016

Related U.S. Application Data

(63) Continuation-in-part of application No. PCT/DE2014/000357, filed on Jul. 16, 2014.

(30) Foreign Application Priority Data

Jul. 17, 2013 (DE) .................. 10 2013 011 870
Aug. 14, 2013 (DE) .................. 10 2013 013 565

(51) Int. Cl.
*A61C 8/00* (2006.01)
*A61C 13/20* (2006.01)

(52) U.S. Cl.
CPC .......... *A61C 8/0059* (2013.01); *A61C 8/0048* (2013.01); *A61C 8/0068* (2013.01); *A61C 8/0077* (2013.01); *A61C 8/006* (2013.01); *A61C 13/206* (2013.01); *A61C 2008/0046* (2013.01)

(58) Field of Classification Search
CPC ....... A61C 8/00; A61C 8/0059; A61C 8/0077; A61C 8/0068; A61C 8/0048; A61C 8/006; A61C 8/005; A61C 13/206; A61C 13/00; A61C 2008/0046; Y10T 29/49567; Y10T 29/49945; Y10T 29/49886
See application file for complete search history.

(56) References Cited

U.S. PATENT DOCUMENTS

| 2002/0168613 A1* | 11/2002 | Riley | A61C 8/0048 433/173 |
| 2009/0258327 A1* | 10/2009 | Zipprich | A61C 8/0012 433/173 |
| 2011/0200969 A1* | 8/2011 | Schroering | A61C 8/0018 433/174 |
| 2013/0260339 A1* | 10/2013 | Reddy | A61C 8/0006 433/174 |

FOREIGN PATENT DOCUMENTS

DE        202012102746 U1 *  8/2012  ............. A61C 8/005

OTHER PUBLICATIONS

English Machine Translation of DE202012102746U1, Gadu et al., Aug. 22, 2012.*

* cited by examiner

*Primary Examiner* — Sarang Afzali
(74) *Attorney, Agent, or Firm* — Klaus J. Bach

(57) ABSTRACT

A superstructure support for disposition between an implantation body and a crown of a prosthetic tooth replacement includes a crown supporting area with an upper engagement structure or supporting the crown and a lower area facing the implantation body and having a smooth microstructure surface provided with webs and grooves extending around the superstructure support and acting as bacteria barrier between the gum of a patient and the superstructure support when mounted onto the implantation body installed in the jawbone of the patient.

6 Claims, 5 Drawing Sheets

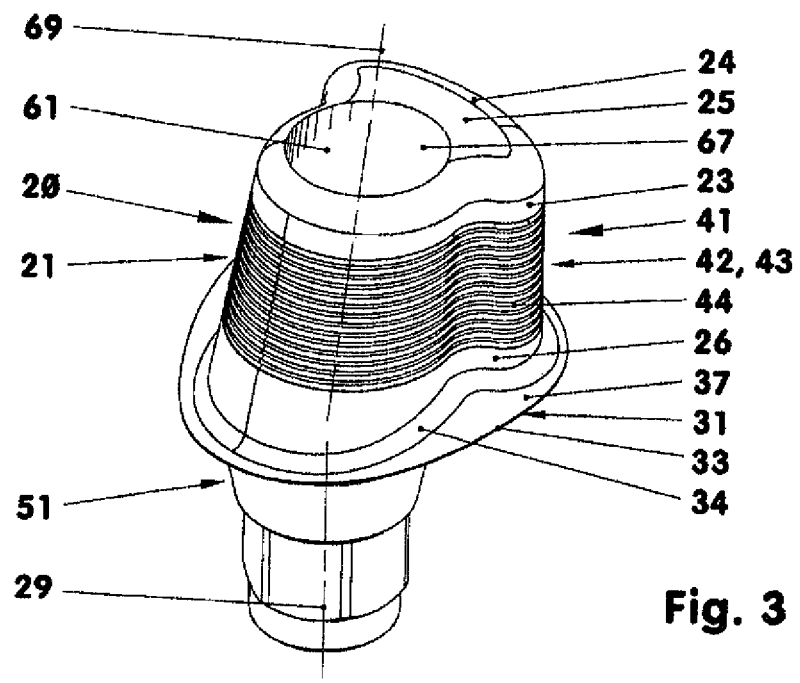
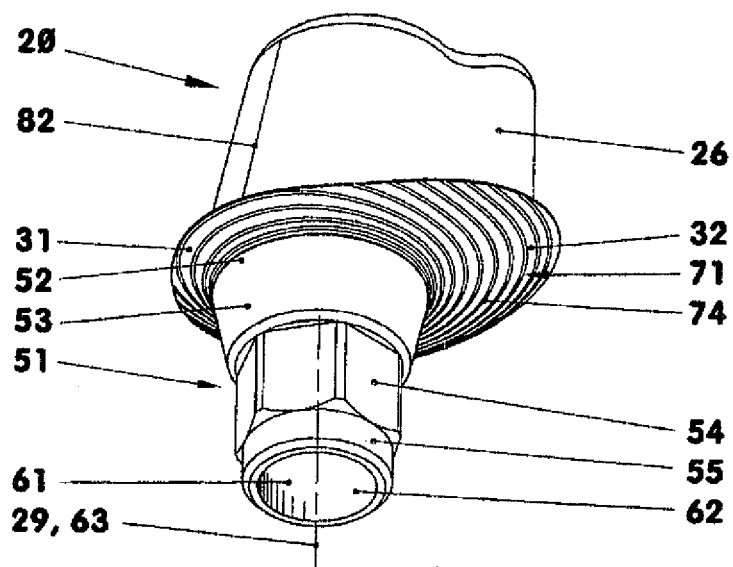
Fig. 3
Fig. 4

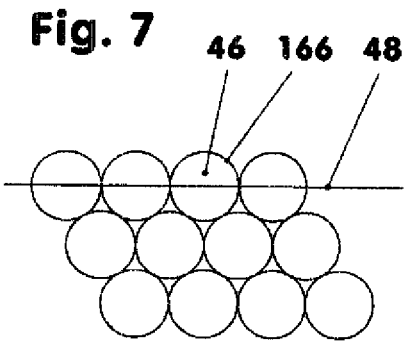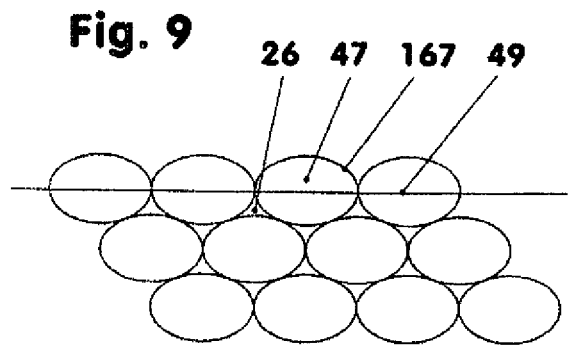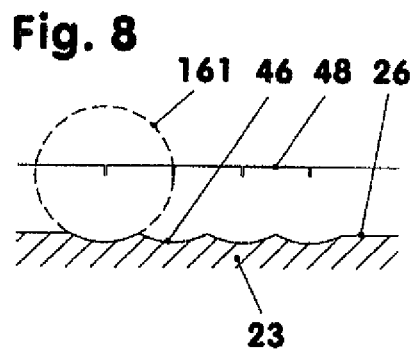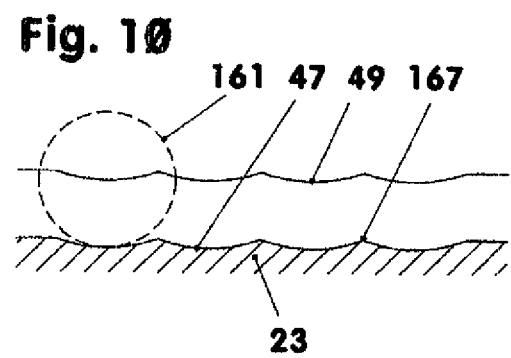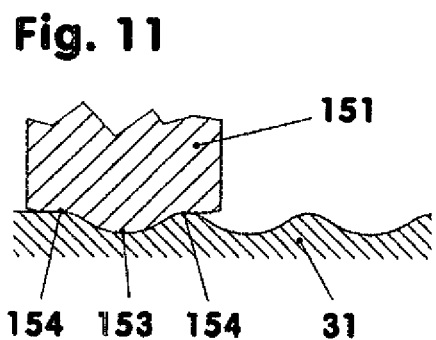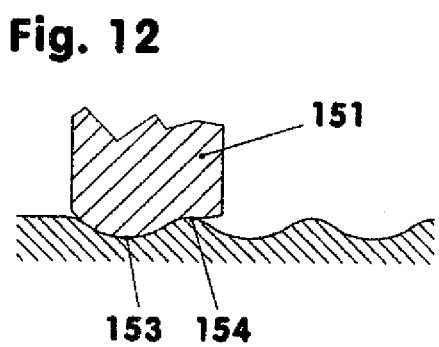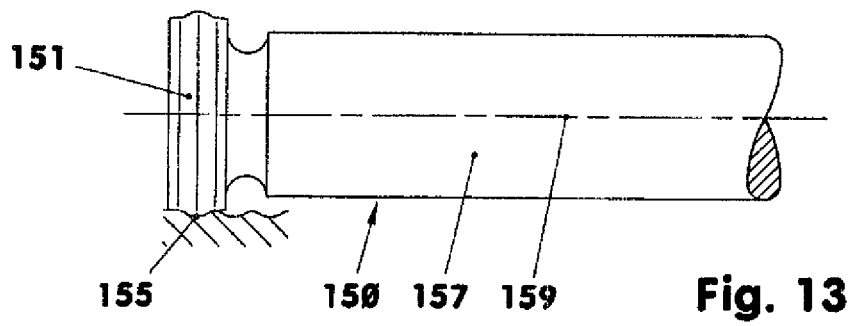

DENTAL IMPLANT SUPERSTRUCTURE SUPPORT

This is a Continuation-In-Part application of pending international patent application PCT/EP2014/00357 filed 2014 Jul. 16 and claiming the priority of German patent applications 10 2013 011 870.0 filed 2013 Jul. 17 and 10 2013 013 565.6 filed 2013 Aug. 14.

BACKGROUND OF THE INVENTION

The invention resides in a superstructure support and a method for producing the same as part of a prosthetic tooth replacement between an implant body and a superstructure consisting of an artificial crown or a composite of a cement body and a crown arranged on the superstructure support.

In the dental implantation technology, in the production of a prosthetic replacement of a single tooth, often an enossal implantation body is used which supports the prosthesis. In this case, the implantation body in the form of a threaded dowel is screwed into a bore which has been formed into the jaw bone of a patient. Into the implantation body which has been screwed into the jaw bone an implantation post is inserted when the prosthesis is finished. The implantation post is for example screwed into the implantation body by means of a special screw so that it is non-rotatably mounted. Onto the implantation post the superstructure which forms the visible tooth crown is directly or indirectly mounted for example by cementing.

It is the object of the present invention to provide an improved superstructure support and an improved method for producing a prosthetic tooth replacement so that, with an effective manufacture, on one hand, the superstructure is safe to wear and, on the other hand, the tooth replacement securely adheres to the gum.

SUMMARY OF THE INVENTION

In a superstructure support and a method for producing same as part of a dental prosthesis disposed between an implant body and a superstructure, an artificial crown or a composite of a cement body and a crown is arranged on the superstructure support which is provided with a crown supporting structure. A second structure is additionally provided on the superstructure support in the region thereof facing the implant body. The support structure support is produced by a powder injection casting method with structured support surfaces such that a secure support of the superstructure and secure adhesion of the dental prosthesis to the implant body and the gum are ensured.

The superstructure support is arranged between an implantation body and a superstructure wherein the superstructure support is provided, in a cement body- and/or crown supporting area, with an implantation post and in the area facing the gum and the implantation body, with at least one implantation neck. The superstructure support is manufactured from a blank which has been produced by means of a powder injection molding method. By means of the powder-injection casting, the blank is molded in the area facing the gum and the implantation body with a shape which is mathematically close to a desired final shape so as to form an unfinished plug. In the area facing the gum and the implantation body the injection molding die provides for a shape of an unfinished lug. The unfinished lug is provided, by mechanical and optical machining, with its finished shape wherein, facing the gum, an implantation plate is formed into whose surface facing the gum at least in areas a certain structure is machined.

During powder injection casting, a metal—or ceramic powder mixed with a thermoplastic binder is injected under pressure into a heated injection mold. After removal of the mold, the binder of the blank is removed by baking or by chemical dissolution, at least to a large extent. Finally, the blank with the binder removed is sintered in an oven until it has the required material density. During this process, the geometric dimensions of the blank shrink about proportionally by 5-35 percent which has to be taken into consideration. As metal powder for example the titanium alloy Ti6Al4V is used which has a shrinkage rate of 7 to 12%.

It is of course also possible to produce the blank in a 3D printer suitable for use with metal or ceramic powder. Also, a manufacture in a die or in a spark erosion machine is possible.

The invention will become more readily apparent from the following description of schematically presented embodiments.

BRIEF DESCRIPTION OF THE DRAWINGS

FIG. 3 shows a superstructure support with post-side structure;

FIG. 4 shows a superstructure support with neck-side structure;

FIG. 7 is a top view of the structure with spherical recesses in the implantation post;

FIG. 8 is a cross-sectional view of FIG. 7 with a cutting head (in dashed line) and the cutting path;

FIG. 9 is a top view of the structure with elliptical recesses in the implantation post;

FIG. 10 is a cross-sectional view of the structure according to FIG. 9 with cutting head (in dashed line) and the cutting path;

FIG. 11 is a cross-sectional view of the furrow-like structure at the bottom side of the implantation plate with a roller tool;

FIG. 12 is a cross-sectional view of the furrow-like structure at the bottom side of the implantation plate with a roller tool which is narrower than that shown in FIG. 11;

FIG. 13 shows the roller tool according to FIG. 11 with a cross-sectional representation of the furrow-like structure according to FIG. 11.

DESCRIPTION OF AN EXEMPLARY EMBODIMENT OF THE INVENTION

Figure 1:
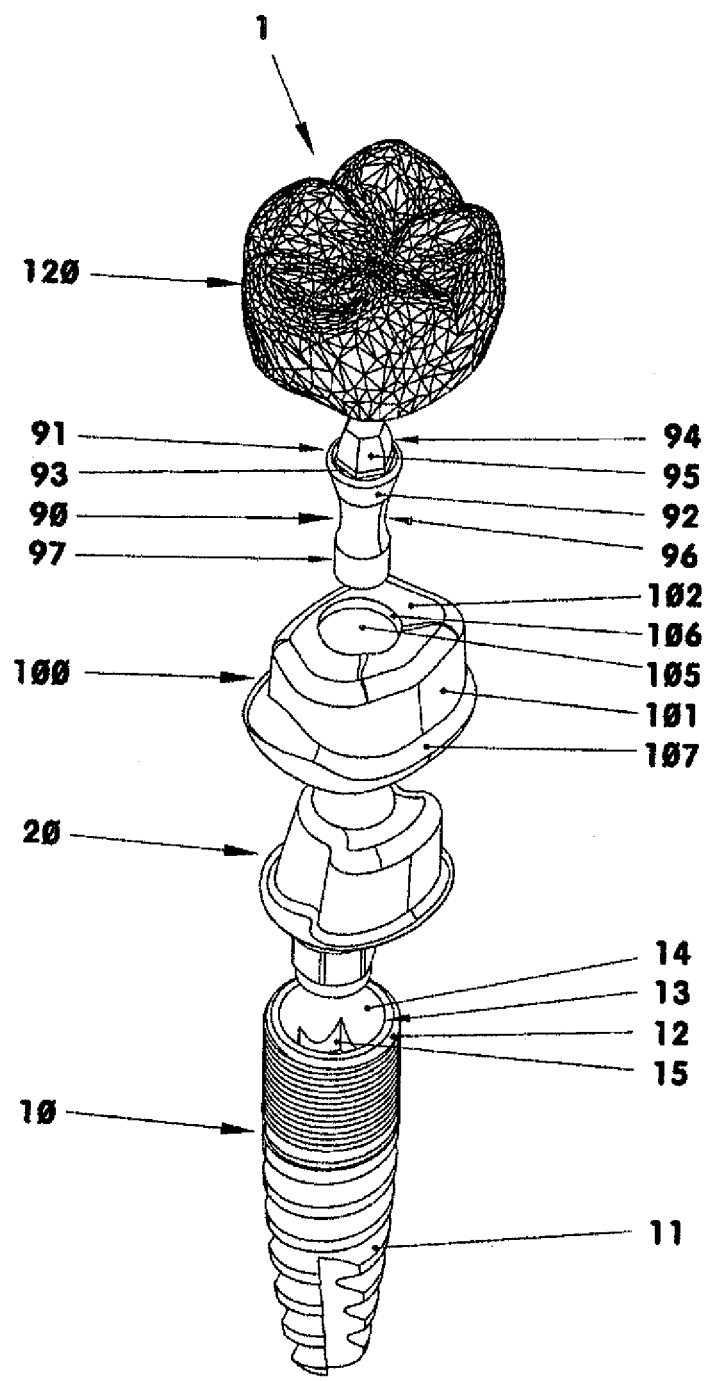
FIG. 1 is an exploded representation of a prosthetic tooth replacement.

FIG. 1 shows in an exemplary manner all parts of an artificial tooth (1) in an exploded view. As base serves a hollow screw-like implantation body (10). Into this implantation body (10), a superstructure support (20) in combination with a cement body (100), which may be cemented to the superstructure support, is screwed by means of an outer hexagon screw (90) so as to be rotationally fixed thereto. Onto the cement body (100), generally, an artificial tooth crown (120) is cemented.

Figure 2:
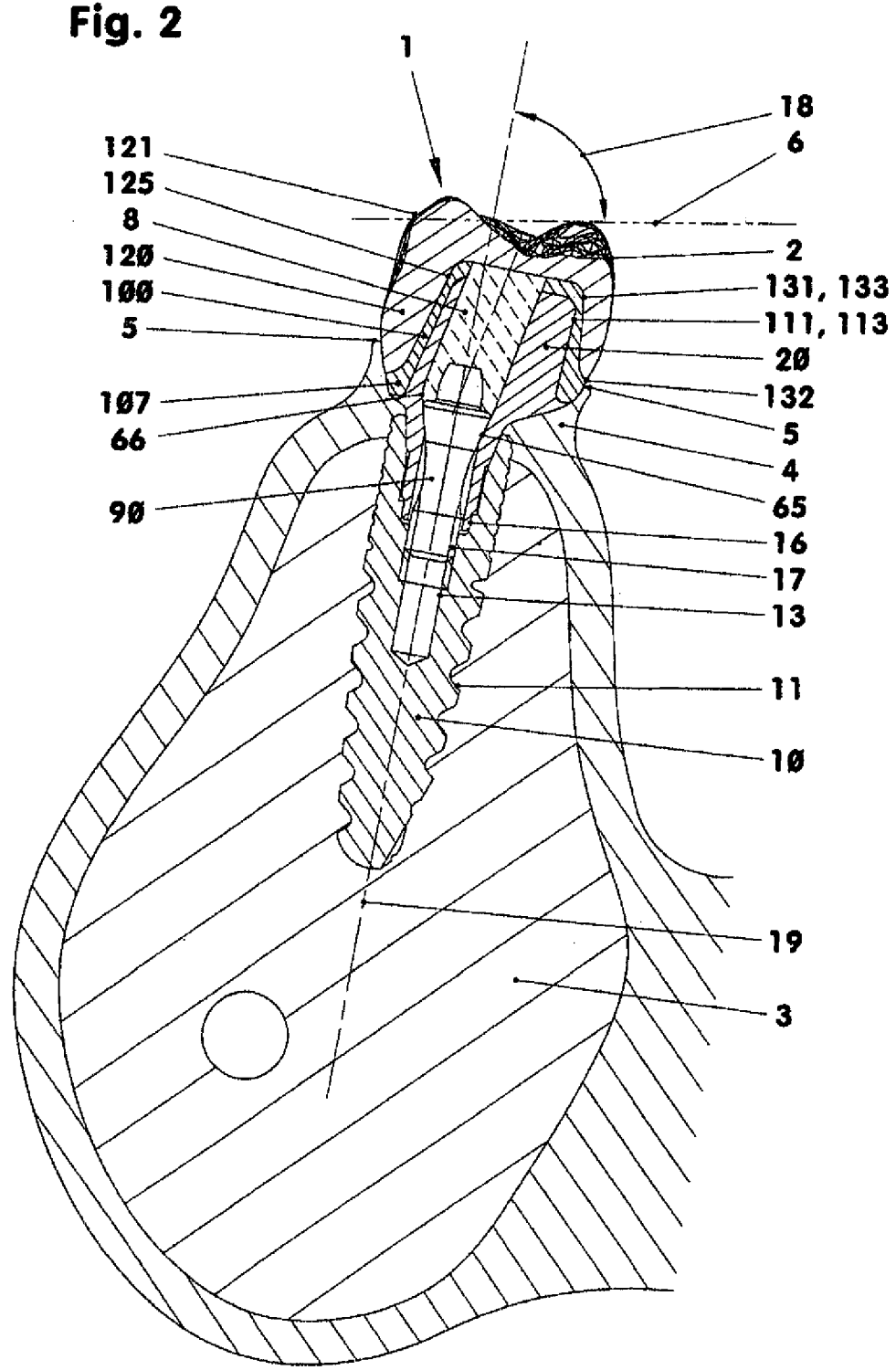
FIG. 2 is a longitudinal cross-sectional view of a prosthetic tooth replacement.

FIG. 2 shows the prosthetic tooth replacement (1) which is built up on an implantation body (10) screwed into a jawbone (3). The jawbone cross-section shown is disposed—as seen from the patient—in the area of the molar teeth at the right jaw side. The cross-section extends normally with respect to the chewing plane (6).

In the implantation body (10), whose centerline (19) extends at an angle (18) of for example 80° with respect to the chewing plane (6), a superstructure support (20), see FIGS. 3 and 4, is disposed in a conical seat (14) so as to be angled with respect to the implantation body (10). The superstructure support (20) is retained in the opening (13) of the implantation body (10) by means of a special hexagonal head screw (90). Onto the cement body (100) attached to the superstructure support (20), a further superstructure part in the form of an artificial tooth crown (120) is cemented.

In accordance with FIGS. 1 and 2, the implantation body (10) is a hollow screw with a self-threading for example non-metric outer thread. About in the upper half, the implantation body (10) has a multi-step cavity (13) which is divided into three zones. The first zone (14) which is disposed in the area of the implantation shoulder (12) of the implantation body (10) in in the form of an internal cone with a cone angle of for example 18 angular degrees, see FIG. 1. The internal cone (14) converges into an internally hexagonal area (15) of the second zone serving as a rotational lock. The internal hexagonal area (15) which may also be in the form of a double internally hexagonal or another form of force-locking rotationally locking geometric structure, a cylindrical seat (16) follows which provides for a centering of the superstructure support (20) in the implantation body (10). The cylindrical seat (16), which may only have a length of for example 0.7 mm, has in this case a diameter which corresponds to the width of the internal hexagonal area (15).

The third zone (17) is a threaded bore into which the special hexagonal head screw (90) is threaded for mounting the superstructure support (20).

The superstructure support forms—disposed in the implant body (10)—the basis for the artificial tooth crown (120). It has an area (51) facing the implantation body (10), see FIG. 3, and an area (21) facing the tooth crown (120) or, respectively, the superstructure, see FIG. 4.

The area (51) facing the implantation body (10) is the implantation neck (52) with its outer cone (53), its outer hexagonal area (54) and for example a short cylindrical extension (55). The outer cone (53), the outer hexagonal area (54) and the cylindrical extension (55) are fitted into the cavity (13) of the implantation body (10). In the axial direction pointing toward the tip of the implantation body (10), the front surfaces of the areas (54,55) are not in contact with the recess (13).

On top of the implantation neck (52), there is an implantation plate (31) which emerges continually and extends smoothly from the implantation neck (52), see FIG. 4. The implantation plate (31), which may for example be out of round, is provided, at least in areas, with the shape of a truncated cone whose cone angle opens toward the tooth crown (120). The cone angle is for example 125 to 131 angular degrees. The underside of the implantation plate (31) may also have the form of several conical areas arranged on top of one another wherein each one is provided with a different cone angle with respect to its centerline. In this case, the cone angles are between 120 and 136 angular degrees.

The edges formed thereby between adjacent cones may also function as bacteria barriers if the angle formed by the adjoining circumferential flanks—as measured in the space outside the implantation plate (31)—is larger than 180 degrees.

In the shown embodiment the outer edge (33) of the implantation plate (31) has a distance from the centerline (29) which, in a 360° turn around the centerline (29), continually changes between 2.22 and 3.48 mm. The edge (33) is subjected hereby in the longitudinal direction of the centerline (29) to an elevation change of for example 0.78±0.2 mm.

As shown in FIG. 4, the underside (32) of the implantation plate (31) has a groove-structure 71. The individual grooves (74) of the structure (71) are formed for example by a cutting or grinding process. Herein, for example the center point of the head of the cutting or grinding tool such that the spherical head of a dental drill may be guided on a plane which extends normal to the center axis (29). Each groove (74) formed by the cutting or grinding tool follows a closed path extending continually around the center axis.

In place of the plurality of grooves 74, only a single groove may be provided which extends circumferentially spirally along the underside (32) of the implantation plate (31).

As shown in FIG. 4, the grooves (74) are so spaced from one another that, between them, areas or webs remain which correspond for example to the width of a single or several grooves. However, the grooves may also be provided without any space between them. In this case, an edge-like projection is formed between two adjacent grooves. In a direction transverse to the longitudinal extension thereof, the individual groove has a circle-section-like cross-section. The distance between the edge-like projections formed by three grooves then corresponds to the mathematical length of a secant s of this circle section-like cross-section. The depth of the groove corresponds to the mathematical height of the arc h. The relationship of the height of the arc h and the length of the secant s based on the radius of the cutting tool r is defined by the formula $$h = r - (r^2 - 0.25 \times s^2)^{1/2}$$

Considering several adjacently arranged grooves whose edge-like projections have a distance of s from one another, the so-called pitch, h defines the amplitude disposed between the groove bottoms and the edge-like projections (=webs). The amplitude h and the distance s define the macrostructure of the surface.

With a ball head cutter with a radius of 0.5 mm and a pitch of 100 μm an amplitude of about 2.5 μm is calculated. If, with an unchanged radius, the pitch is doubled, the amplitude is increased to about 21 μm. The pitch is preferably between 80 and 250 μm.

For the surface of the underside two requirements are postulated. On one hand, the surface should have continually circular projections or webs or grooves formed into the surface. With these projections, webs or grooves, circular edges are formed which act as bacteria barriers. The distance between adjacent edges (=edgy projections) is for example 0.1 to 0.5 mm. On the other hand, the surface as such should be mirror-like smooth in order to avoid, already for physical reasons, a short-term or durable attachment of bacteria.

To this end, the arithmetic average roughness value in the area of the underside (32) of the implantation plate (31) and on the implantation neck (52) should be in the range of only 1.5 to 3.0 μm in spite of the microstructure (71). In this way, the "wavy" underside (32) provided with miniature barriers has on the wave tops and wave bottoms an almost pore-free closed surface.

Instead of a cutting machining of the underside of the implantation plate (31) and the implantation neck (52) a deforming treatment may be provided. It is for example possible to impress the grooves into the surface by a roller tool. The so-called rolling provides for a fine-machining generating a groove depths of less than 1 μm. In addition to a smooth surface obtained thereby the workpiece surface is also hardened.

FIGS. 11 and 13 show such a rolling tool (150) which has a profile by which the wave bottoms are impressed and the wave tops are smoothened. To this end, the roller head (151) of the roller tool (150) has a groove profile section (153) with a smoothing section (154) arranged at opposite sides of the groove profile section (153). The groove profile section (153) provides for the corresponding wave bottoms. The smoothing sections (154) are recessed at the free ends in order to avoid the formation of rolling edges. In the area of the recesses, the radii of the roller tool with respect to the centerline (159) becomes smaller with increasing distance from the center of the roller head (151).

FIG. 12 is a cross-sectional view of part of a roller head (151), which does not have a smoothing section (154) at its end remote from its shaft.

During the rolling process, the roller tool (150) is oriented with respect to the structure support in such a way that the radial line extending between the roller contact point (155) and the center line (159) is disposed normal on the surface of the underside (32) which has not yet been rolled. At the same time, the plane extending normal to the center line (159) in which the radial line is disposed extends tangentially to the path curve of the wave bottom.

Instead of a roller tool rolling on the workpiece also a diamond smoothing tool may be used. In this case for example a semi-circular diamond is pulled along the path curve for grooving and smoothing the surface.

With the shown roller tool (150) only one groove is formed with each rotation. But it is of course also possible to combine several roller heads (151) in a single forming tool. With such a forming tool then all the grooves can be formed at the same time in single rotation. And since the individual grooves are formed at different radii, there is necessarily a certain slippage which has a smoothening effect. The possibility to use a forming tool with several rolling heads may also be transferred to the use of a cutting tool. In this case, a form—or profile cutter machines all or at least a group of several grooves at the same time in a single turn or orbit.

Alternatively to the described annular structures, it is also possible to machine stochastically distributed depressions or dents into the underside (32) of the implantation plate (31). To this end, among others the glass beaming procedure is suitable. Herein, glass pearls with a diameter of 15 to 50 μm are shot with pressurized air via a nozzle onto the object to be machined.

Above the implantation plate 31, there is in the area (21), the implantation post (23) which has for example in a rounded transition area (34) to the implant plate (31), a cross-section which is smaller than the largest cross-section of the implantation plate (31). As a result, also the implantation plate (31) has adjacent the implantation post (23) an areal edge surface (37). In almost any sectional plane extending through the centerline (29), the contour of the areal edge top side is oriented at least in some areas normally with respect to the centerline (29). At the most narrow location, the implantation plate (31) projects radially by 0.4 to 0.5 mm. The widest area may be more than 2 mm wide. The areal edge top side (37) forms among others a seating surface for the cement body (100) or the tooth crown (120).

Figure 6:
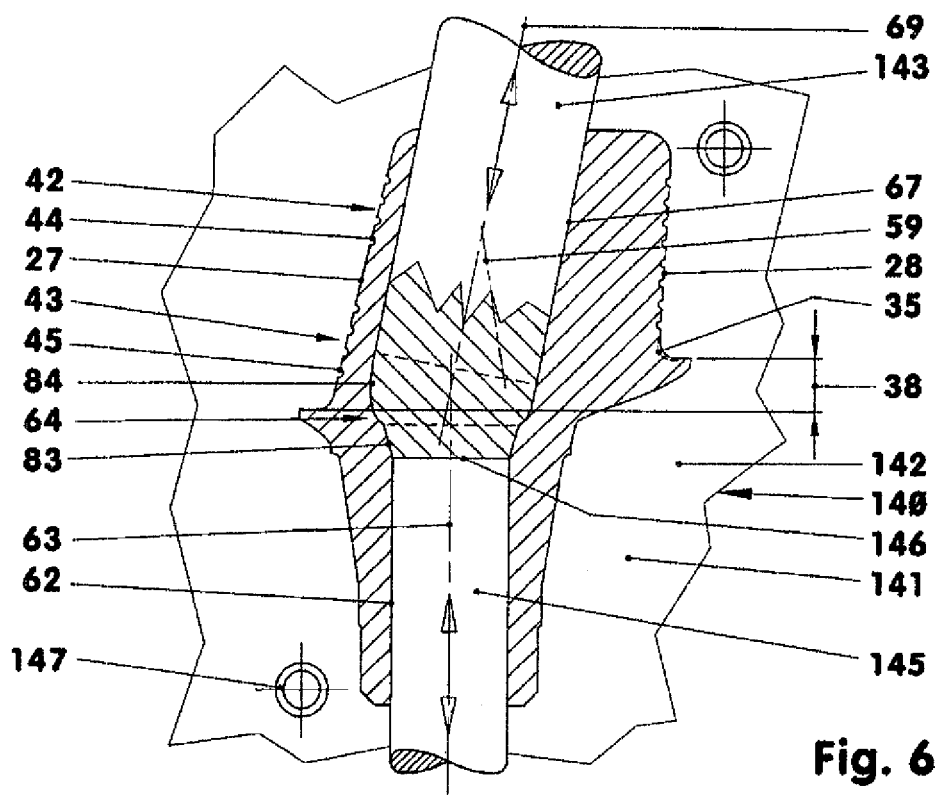
FIG. 6 shows a longitudinal cross-section of FIG. 5 with parts of an injection molding die.

The rounded transition area may also be deepened in axial direction parallel to the center line by 0.05 to 0.2 mm, so that between the areal upper side of the edge (37) and the implantation post (23) a groove (35) is formed (see FIG. 6, dashed line).

The generally 3 to 4 mm high implantation post (23) has in accordance with the cross-sectional view of FIGS. 2 and 6, a trapezoidal cross-section. Above the implantation plate (31), the left flank line (27) is inclined toward the center line (29) for example by 13.3 angular degrees, wherein the virtual extension of the right flank line (28) intersects the centerline (29) far below the implantation plate (31).

In the upper area, the flank lines (27, 28) transition to a horizontal line as shown in FIG. 6. This line represents the main support surface (25), see FIG. 3, which ideally extends normal to the center axis (29)—at least as long as the superstructure has not yet been machined by a dental technician.

In a direction transverse to the intersection shown in FIG. 6, the implantation post (23) narrows down toward the top. Its flank lines extend there generally at an angle of 3±0.5 angular degrees with respect to the centerline (29). However, the implantation post may also have flank lines which extend parallel to the center line (29).

As shown in FIGS. 1 and 4, the implantation post (23) consists approximately of an inclined truncated cone with a circular base cross-section and an inclined truncated cone section with an elliptical cross-section which partially penetrates the truncated cone with circular cross-section. The center lines of the two truncated cone section define a plane in which the small semi-axes of the elliptical cross-section are disposed. In the penetration areas of the two inclined truncated cones, there are rounded structures whose radii are between 0.3 and 0.4 mm.

With this special form of the implantation post (23), a rotationally fixed basis for the cement body (100) to be supported thereby is provided.

The radial outer surface area (26) of the implantation post (23) supports in accordance with FIG. 3 a structure which consists for example of a multitude of parallel grooves 44. Each of the grooves is disposed in a plane which is oriented normal to the centerline (29). The uppermost groove is spaced from the main support surface (25) by for example 0.5 mm. The structure (41) is disposed at a height of for example 2.5 mm. Each groove (44) has a maximum depth of 0.005 to 0.025 mm. The depth in this case is the shortest distance between an enveloping surface area around the implantation post (23) and the deepest point of the respective groove. It is between 1 and 35 μm. The enveloping surface area is the imaginary surface area which corresponds to the theoretical radially outer surface area (26) before the cutting of the grooves.

In accordance with FIG. 6, the structure is divided into two areas (42, 43) which are angled relative to each other. The upper area (42) exhibits grooves which are arranged on the implantation post (23) in a manner comparable to FIG. 3. The lower area has grooves (44) which extend in planes with normal lines thereof that are tilted with respect to the centerline (63) by 9±1 angular degrees. The inclination is so selected that the grooves extend parallel or almost parallel to the upper surface (37) of the implantation plate (31). It is of course also possible to arrange the individual grooves (44) on the implantation post in such a way that they extend in planes which are angled relative to one another. In this case, adjacent grooves are spaced from each other at a smaller distance along the right flank line (28) than they are at the left flank line (27). It is also possible that at least some of the grooves intersect.

Alternatively, instead of multitude of grooves (44) only one groove may be used which extends spirally or thread-like with or without interruption along the radially outer surface (26) of the implantation post (23). The grooves (44, 45) can be formed in the same way as the grooves (74), see above.

In accordance with FIGS. 3 and 6, the grooves (44, 45) are spaced in such a way that, between them, areas or webs remain which have a width corresponding for example to the width of the grooves. However, the grooves may be arranged also next to one another without spaces therebetween.

In order to produce for example a groove (74) or a track (48) whose depth and/or width changes cyclically, for example a ball head cutter with only a small number of teeth is moved along the radially outer surface (26) of the implantation post (23). The center line of the cutter extends then with respect to the center line (29) at an angle of 15±20 angular degrees with a predetermined advance/rotational speed ratio a structure is formed on the outer surface which corresponds essentially to the surface pattern of golf ball, which is provided with depressions called dimples, see FIG. 7. The dimples are in accordance with FIGS. 7 and 9 the depressions (46, 47) whose edges are seen on the outer surface (26) for example as continuous curves (166, 167). The closed curves (166) have in a vertical top view almost the form of a circle whereas the closed curves (167) appear in a vertical top view almost as ellipses.

FIGS. 8 and 10 show in each case an example of how the depression (46, 47) can be formed. For simplification, the outer surface (26) is chosen to be planar. Along the outer surface, a cutter is moved whose cutting head (161) is guided first parallel along the surrounding surface (26). The guide line (48) has from the surface (26) for example a distance which corresponds to the radius of the cutting head (161). As soon as the cutting head (161) is disposed over the center of the depression to be formed the cutting head (161) dips into the outer surface (26) of the implantation post (23) while removing some material. After reaching the respective depth, it is retracted by the dipping amount and is then moved parallel to the outer surface (26) to the next cutting point.

As shown in FIG. 10, the cutting head moves along a wave-like curve 48 in order to generate the depressions (47) with the almost elliptical edges (147) and a longitudinal extension of 0.3 to 1.1 mm.

In both cases, a structured surface is generated whose depressions may have for example also a depth of 1-20 µm. The individual depression which may be for example spherical ellipsoidal or also elongated hole-like, has a diameter or a length between 1 and 1000 µm. In an exemplary embodiment, not shown, the depth is 2.5 µm with a diameter of 100 µm.

The geometric values of the microscopic structure (41) are among others a function of the size of the particles of the cement material (113) by which the implantation post (23) and the cement body (100) are joined. If the particle size is between 1 and 20 µm and the gap of the cementing joint (111) has a width of 10 to 35 µm, in spite of the cement material jointure in the area of the structure (41) a kind of form-locking is achieved as a result of the depressions or, respectively, grooves (44, 45) in which the larger particles of the cement (113) are contained.

In addition, the superstructure support (20) is provided at least above the implantation plate (31) with a titanium-nitride coating. The coating has a thickness of for example 1 to 4 µm. Alternatively, a thin-walled ceramic or copolymer coating may be applied.

As shown in FIGS. 1, 3 and 4, the superstructure support (20) has an opening (61) which extends all the way therethrough and which has, in the center area thereof, a bend with an angle of 11±4 angular degrees. The finally machined opening (61) comprises three zones. A lower zone (62) is a cylindrical bore with a diameter of for example 1.7 mm. Its center line (69) is the same as the center line (29). In accordance with FIG. 1, the shaft (96) extends through the lower zone (62) of the hexagonal head screw (90) while the shaft (96) does not come into contact with the wall of the lower zone (62).

The upper zone (67) is also a cylindrical bore. Its center line (69) intersects the intermediate zone (64) at an angle of, in this case, 11 angular degrees. The upper zone (67) permits the insertion of the hexagonal head screw (90) and also serves as guide for the tool by which the hexagonal head screw (90) is tightened. The intermediate zone (64) is a transition area which is provided with an internal, conical area (65) and also has an inclination area (66), see FIG. 2. The internal conical area (65), which is coaxial with the lower zone bore (62), serves as engagement surface for the head (92) of the hexagonal head screw (90). A screw insertion opening (61) is provided in the implantation post (23) which extends with respect to the lower zone (62) in the implantation neck (52) at an angle of 155-178 degrees with respect to an axis (69) of the superstructure support (20).

The inclination area (66) adapts the cylindrical bore of the upper zone (67) at the inclination point to the large opening cross-section of the inner conical area (65). The transition is provided in the exemplary embodiment without edges that is tangentially.

FIG. 6 shows in a longitudinal cross-sectional view a blank (80) which is being manufactured by a powder injection casting process to form the superstructure support 20 disposed in an opened injection molding die (140). The injection molding die (140) consists essentially of two die halves (141) and two slides (143, 145). The front faces of the slides (143, 45) are in contact with each other along a separation seam (146).

Figure 5:
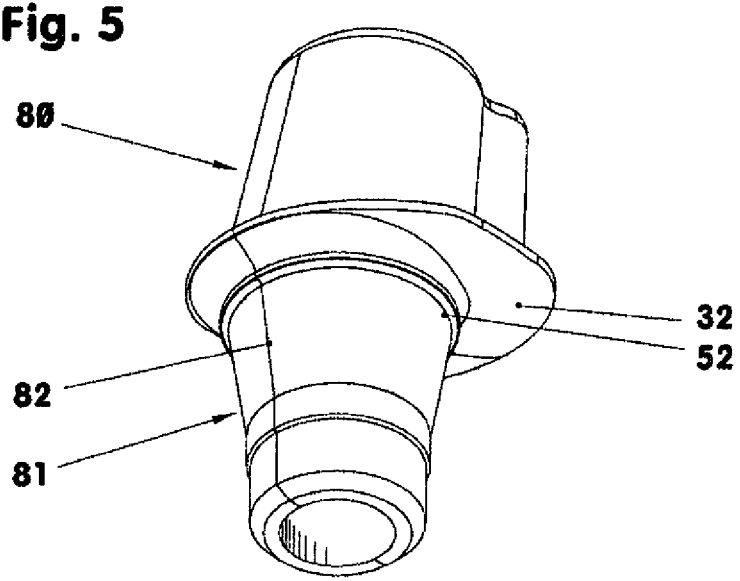
FIG. 5 shows a blank of a superstructure support.

The separation plane (142) of the die halves (141) is disposed in FIG. 6 in the drawing plane. The outer separation line (82) formed by the two die halves that is the respective seam is shown in FIG. 5 as a line.

The injection casting die (140) provides generally for the final shape of the superstructure support (20) above the implantation plate (31) or, respectively, the edge top side (37). Accordingly, the grooves (44, 45) and the depression (46, 47) may also be formed by means of the structure of the injection casting die (140) or, respectively, the die halves (141). An alternative method of producing a structure of the size as described resides in providing in the area above the implantation plate (31) powder with an increased particle size of for example 10 to 50 µm. This results even with dies (40) with smooth walls in the formation of stochastically distributed depressions with depths that may reach 10 to 30 µm.

It is possible to provide on the superstructure support (20) in the area of its upper edge top side (37) or in the area of the main support surface (25) or nearby a pin-like extension in order to facilitate handling of the component by a dental technician before the machining thereof.

Below the upper edge side (37), the superstructure support (20) is provided with a preliminary shape which needs to be machined at a later time. Such a later machining is necessary among others for the bottom side (32) of the implantation plate (31), the implantation cone (53), the outer hexagonal area (54) and the cylindrical extension (55).

The upper slide member (143) provides for the final form of the upper zone (67) of the opening (61) whereas in the intermediate zone (64) only a preliminary rough shape of a projection (81) is formed. The intermediate zone (64) is formed with a reduced size internal cone (83) and a shortened tilt angle range (84). The inner cone (83) and the tilt angle range (84) are provided with their final shape shown in FIG. 2 later by fine machining. The cutting tool is introduced for that purpose via the lower zone (62) which is formed by means of the lower slide member (145). During fine machining also, the cylindrical bore of the lower zone (62) is drilled out to its design dimensions.

The external hexagonal head screw (90) comprises three areas that is a head area (91), a shaft area (96) and a thread area (97), see FIGS. 1 and 2. The head area (91) consists of a cone-like head (92) with a tool engagement structure (94) arranged on top of it. The head (92) has a height of for example 1.28 mm and the form of a truncated cone which narrows down toward the thread area (97) with a cone angle of 30 angular degrees. The cone-like area via which the head screw (90) is in contact with the superstructure support (20) has a length of for example 1.09 mm. Its largest diameter is 2.2 mm.

The tool engagement structure (94) has the shape of an external hexagon onto which, for tightening the screw (90), a tubular internally hexagonally-shaped range is placed. The external hexagon narrows down at least in the last two thirds of its length toward the top end of the head. The external hexagon has a maximum range width of 1.42 mm. The area of this maximum width is arranged for example 0.29 mm above the upper head front surface (93). The curvature radius of the hexagon flanks (95) is for example 2.36 mm.

Next to the cone-shaped area of the head (92) follows the second area that is the shaft area (96). The shaft area (96) comprises a rotationally symmetrical axial center area, which is disposed for example 3.8 mm from the top end of the head area (91) and has in the axial center a smaller diameter of for example 1.28 mm. The curvature of the outer contour of the axial center area has as shown in FIG. 2 a radius of 5.2 mm.

The third area is the thread area (97). It is provided with a M1,6 thread, whose usable length is for example 1.5 mm.

In the exemplary embodiment, a cement body (100) is cemented onto the superstructure support (20). The cement body (100) is a hollow body which is arranged within the tooth prosthesis between the support structure support (20) and the artificial tooth crown (120). It serves for example to adapt the angular position of the tooth crown (120) to the angular position of the implantation post (23).

The cement body (100) is essentially pot-shaped. Its internal wall (105) is adapted to the outer wall (26) of the implantation post (23) including the edge surface side (37). There is for example a 30 to 50 μm clearance so that the cement body (100) is disposed with a large surface area on the implementation post (23) of the superstructure support (20) with a cement layer (113) disposed therebetween. The cement layer (113) also attaches firmly to the implantation post (23) in a form-fitting manner as a result because of the upper structure (41) of the implantation post (23).

The cement body (100) has a widened rim (107) via which it is supported on the top side (37) of the superstructure support (20) and, at the same time, provides support for the crown or at least areas thereof.

In the area of the top side (102), the superstructure support (20) includes an opening (106) which, with the prosthesis mounted, forms an extension of the opening of the upper zone (67) of the implantation post (23).

As shown in the exemplary embodiment, the tooth crown (120) is disposed on the cement body (100). Accordingly, the inner wall (125) of the tooth crown (120) is adapted to the outer wall (101) of the cement body (100). Also, in this case, the clearance between the outer wall (101) and the inner wall (125) is 20 to 50 μm. The cement body (100) and the tooth crown (120) are formed in the area of the edge (132) of their cementing seam (131) in such a way that the last tenth millimeter meets the common prosthesis outer surface (2) at an angle of 90±10 angular degrees. In the edge area of their cementing seam (131), the outer surface area (121) of the tooth crown (120) and the outer surface area (101) of the cement body (100) are joining each other tangentially or at least almost tangentially. If there is a bend-over the enclosed angle is in a range of less than 180 and larger than 175 angular degrees.

As shown in FIG. 2, the superstructure support (20) of the finished prosthesis is disposed non-rotatably by means of an implantation cone (53) in the conical seat (14) of the implantation body (10) and is screwed thereto. The implantation neck (52) and the underside (32) of the implantation plate (31) abut the gum (4). The bottom side (32) which is provided with a structure (71) which forms a barrier for bacteria reduces or prevents bacteria from developing in the interface area between the implantation plate (31) and the gum (4). In addition, the structure (71) facilitates the attachment of the connective tissue fibers of the gum (4) to the superstructure support (20) below the implantation plate (31).

As shown, the combination of cement body (100) and the artificial tooth crown is disposed on the implantation plate (31) and cemented thereto. At the outer side of the tooth, the cementing seams (111) and (131) are disposed protected below the upper gum edge (5). At the lingual or, respectively, inner side of the tooth, at least the cementing seam (111) is covered by the gum (4).

| Listing of Reference Numerals | |
|---|---|
| 1 | Artificial tooth |
| 2 | Outer surface of prosthesis |
| 3 | Jaw bone |
| 4 | Gum |
| 5 | Gum edge |
| 6 | Chewing plane |
| 8 | Cement |
| 10 | Implantation body |
| 11 | Outer thread |
| 12 | Implantation shoulder |
| 13 | Opening, stepped |
| 14 | Inner cone, first zone, cone seat |
| 15 | Inner hexagon structure, second zone |
| 16 | Cylinder seal |
| 17 | Threaded bore, third zone |
| 18 | Implantation inclination angle |
| 19 | Centerline |
| 20 | Superstructure support |
| 21 | Area facing the tooth crown |
| 23 | Implantation post |
| 24 | Upper side |
| 25 | Main support surface area |
| 26 | Outer surface, radial; outer wall |
| 27 | Flank line left |
| 28 | Flank line right |
| 29 | Center line |
| 31 | Implantation plate |
| 32 | Underside facing the gum |

| | Listing of Reference Numerals |
|---|---|
| 33 | Edge |
| 34 | Transition area |
| 35 | Groove |
| 37 | Top side of the edge area |
| 38 | Height displacement |
| 41 | Structure, groove structure |
| 42 | Upper area |
| 43 | Lower area |
| 44 | Grooves |
| 45 | Grooves of lower area |
| 46 | Depressions with round edges |
| 47 | Depressions with oval edges |
| 48 | Centerpoint line of movement |
| 49 | Centerpoint line of movement |
| 51 | Area facing the implantation body |
| 52 | Implantation neck |
| 53 | Implantation cone, outer cone |
| 54 | Rotation lock, outer hexagon |
| 55 | Cylinder extension |
| 59 | Normal line |
| 61 | Screw insert opening |
| 62 | Lower zone; bore, screw accommodation opening |
| 63 | Center line of (62) |
| 64 | Intermediate zone |
| 65 | Inner cone |
| 66 | Angle range |
| 67 | Upper zone, bore |
| 69 | Centerline of (67) |
| 71 | Microstructure, groove structure |
| 74 | Grooves |
| 80 | Blank of the superstructure support |
| 81 | Unfinished pin |
| 82 | Seam path |
| 83 | Inner cone |
| 84 | Inclination area |
| 90 | Hexagonal head screw |
| 91 | Head area |
| 92 | Conical head |
| 93 | Head front area |
| 94 | Tool accommodation |
| 95 | Hexagonal head flanks |
| 96 | Shaft area |
| 97 | Threaded area |
| 100 | Cement body |
| 101 | Outer wall area |
| 102 | Top side |
| 105 | Inner wall surface |
| 106 | Opening |
| 107 | Edge |
| 111 | Cement seam between (23) and (100) |
| 113 | Cement |
| 120 | Tooth crown |
| 121 | Outer wall, outer surface area |
| 125 | Inner wall, inner surface area |
| 131 | Cement seam |
| 132 | Cement seam edge |
| 133 | Cement |
| 140 | Injection casting die |
| 141 | Die halves |
| 142 | Separation plane |
| 143 | Slide member top |
| 145 | Slide member bottom |
| 146 | Separation seam |
| 147 | Centering pin |
| 150 | Roller tool |
| 151 | Roller head |
| 153 | Groove profile section |
| 154 | Smoothing section |
| 155 | Roller contact area |
| 157 | Shaft |
| 159 | Centerline |
| 161 | Cutting head |
| 166 | Closed curve circle |
| 167 | Closed curve ellipse |

What is claimed is:

1. A superstructure support (20) for disposition as part of a prosthetic tooth replacement (1) between an implantation body (10) and a superstructure consisting of an artificial crown (120) or a composite of a cement body (100) and the crown (120), the superstructure support (20) comprising:
a screw insertion opening (61) including three zones extending through from a top surface to a bottom surface of the superstructure support (20);
an upper zone (67) having a cylindrical bore with a centerline (69) proximate to the top surface;
a lower zone (62) having a cylindrical bore with a centerline (63) proximate to the bottom surface;
an intermediate transition zone (64) positioned between the lower and upper zones having an internal conical area (65) coaxial with the centerline (63);
an outer area (51) adjacent the implantation body (10) having an implantation neck (52) including outer cone (53) above which an implant plate (31) is arranged;
a crown-supporting area (21) provided with an engagement structure (41) and an implantation post (23) which includes a screw seating bore (62);
a smooth microstructure surface (71) with an average arithmetic roughness value of 1.5 to 3.0 μm provided with webs or grooves (74) at least partially extending around the superstructure support (20); and
spaced edges acting as bacteria barriers formed between a plurality of adjacent conical areas arranged on top of one another provided at the bottom side (32) of the implantation plate (31) on top of the implantation neck (52),
wherein an angle in the range of 155 to 178 angular degrees is formed between the centerline (69) of the upper zone and the centerline (63) of the lower zone.

2. The superstructure support according to claim 1, wherein the implantation post (23) is provided at its radially outer surface area (26) thereof with adjacent grooves (44, 45) or center point tracks (48, 49) with spaced depressions (46, 47).

3. The superstructure support according to claim 2, wherein the grooves (44, 45) and the depressions (46, 47) each has a depth greater than 1 μm and smaller than 35 μm.

4. The superstructure support according to claim 2, wherein a longitudinal extension of each of the depressions (46, 47) is greater than 0.3 mm and smaller than 1.1 mm.

5. The superstructure support according to claim 1, wherein the webs or grooves (74) each has a pitch greater than 80 μm and smaller than 250 μm.

6. The superstructure support according to claim 1, wherein the superstructure support (20) is formed from a metallic or ceramic powder based on a titanium-aluminum alloy.

\* \* \* \* \*